United States Patent
Kountotsis

(10) Patent No.: US 9,047,605 B2
(45) Date of Patent: Jun. 2, 2015

(54) SYSTEM AND METHOD FOR INSTANTANEOUS FINGERPRINT RECOGNITION AND ANALYSIS RESULTING IN TARGETED OUTPUT

(76) Inventor: Theodosios Kountotsis, East Elmhurst, NY (US)

(*) Notice: Subject to any disclaimer, the term of this patent is extended or adjusted under 35 U.S.C. 154(b) by 839 days.

(21) Appl. No.: 12/804,704

(22) Filed: Jul. 27, 2010

(65) Prior Publication Data
US 2012/0029928 A1 Feb. 2, 2012

(51) Int. Cl.
G06Q 30/02 (2012.01)
G01N 19/00 (2006.01)
G01N 33/00 (2006.01)
G06Q 30/00 (2012.01)

(52) U.S. Cl.
CPC ..................................... *G06Q 30/00* (2013.01)

(58) Field of Classification Search
CPC .... G06Q 30/02; G01M 3/005; G01M 99/008; G01N 13/00
USPC ............ 705/1.1, 14.73; 73/865.8, 865.9, 866; 726/34
See application file for complete search history.

(56) References Cited

U.S. PATENT DOCUMENTS

| | | | |
|---|---|---|---|
| 3,982,836 A * | 9/1976 | Green et al. | 356/370 |
| 4,035,941 A | 7/1977 | Deffner | |
| 5,032,716 A | 7/1991 | Lam et al. | |
| 5,264,822 A | 11/1993 | Vogelman et al. | |
| 5,905,429 A | 5/1999 | Hornstein et al. | |
| 6,337,836 B1 | 1/2002 | Eidelson et al. | |
| 6,924,781 B1 | 8/2005 | Gelbman | |
| 2003/0197853 A1* | 10/2003 | Fenrich | 356/71 |
| 2006/0293956 A1* | 12/2006 | Walker et al. | 705/14 |
| 2007/0271194 A1* | 11/2007 | Walker et al. | 705/80 |
| 2009/0077675 A1* | 3/2009 | Cabouli | 726/34 |

OTHER PUBLICATIONS

Parry, Wynne, "Fingerprint Technique Shows What You've Eaten", in Discover Magazine, Aug. 3, 2007, p. 1-2.*

* cited by examiner

*Primary Examiner* — Sun Li
(74) *Attorney, Agent, or Firm* — Theodosios Kountotsis

(57) ABSTRACT

A fingerprint analysis device is presented including a sensing mechanism including an adhesive member configured to perform at least a chemical analysis of a fingerprint and a sound emitting mechanism for emitting one or more sounds based on the chemical analysis of the fingerprint. The chemical analysis device further performs on-the-spot, substantially instantaneous chemical analysis of received fingerprints and emits or conveys audible and/or non-audible information based on the fingerprints received.

17 Claims, 10 Drawing Sheets

SYSTEM AND METHOD FOR INSTANTANEOUS FINGERPRINT RECOGNITION AND ANALYSIS RESULTING IN TARGETED OUTPUT

BACKGROUND

1. Field of the Related Art

The present disclosure relates to fingerprint recognition technology, and more particularly, but not exclusively, to methods and systems for instant fingerprint recognition, reception, collection, transmission, storage, and/or analysis resulting in targeted audible and/or non-audible output.

2. Description of the Related Art

The need to identify and authenticate individuals is greater today than it has ever been, and is particularly acute for applications such as homeland security, law enforcement, electronic commerce, access control and privacy protection, to name a few.

The use of biometrics in general, and fingerprint recognition in particular, to identify and authenticate humans is a proven method. Biometrics is a group of technologies that provide a high level of security. Fingerprint capture and recognition is an important biometric technology. Law enforcement, banking, voting, retail, and other industries increasingly rely upon fingerprints as a biometric to recognize or verify identity.

Fingerprint identification systems usually involve the use of a computer, which provides an identification probability for a match of a fingerprint to a prerecorded fingerprint held in a database. In this manner, fingerprint recognition devices have been employed for accessing high security areas. Fingerprint scanners are one form of fingerprint recognition devices. Fingerprint scanners having image sensors are available, which capture an image of a fingerprint. A signal representative of the captured image is then sent over a data communication interface to a host computer for further processing. For example, the host computer may perform one-to-one or one-to-many fingerprint matching. Moreover, large numbers of fingerprints are collected and stored everyday in a wide range of applications including forensics, access control, and driver license registration. These fingerprints are kept on file and used to help law enforcement officials identify suspects. In modern times, computers and other electronic devices have made it easy to compare a single fingerprint with a large number of fingerprints.

However, to perform identification and authentication in many of the applications envisaged today, quick and accurate collection of several samples of fingerprints in various environments is important. Thus, there is a need for automated fingerprint recognition, where a large number of fingerprints may be collected and analyzed from various environments or items/products without sacrificing accuracy. Thus, there is a need in the fingerprint recognition art for a technological solution that overcomes at least in part the aforesaid deficiencies.

SUMMARY

The present disclosure provides a fingerprint analysis device including a sensing mechanism including an adhesive member configured to perform at least a chemical analysis of a fingerprint and a sound emitting mechanism for emitting one or more sounds based on the chemical analysis of the fingerprint.

The present disclosure also provides a method of analyzing one or more fingerprints, the method including inputting a fingerprint by contacting an adhesive member; performing at least a chemical analysis of the fingerprint; and emitting one or more sounds based on the chemical analysis of the fingerprint.

The present disclosure also provides a chemical analysis device for performing on-the-spot, substantially instantaneous chemical analysis of received fingerprints and emitting audible information based on the fingerprints received.

The present disclosure also provides a fingerprint analysis system, including a processor; a computer-readable storage medium in communication with the processor, the computer-readable storage medium comprising one or more programming instructions for: inputting a fingerprint by contacting an adhesive member; performing at least a chemical analysis of the fingerprint; and emitting one or more sounds based on the chemical analysis of the fingerprint.

The present disclosure also provides a fingerprint analysis system, including a processor; a computer-readable storage medium in communication with the processor, the computer-readable storage medium comprising one or more programming instructions for: providing a chemical analysis device for performing on-the-spot, substantially instantaneous chemical analysis of received fingerprints and emitting audible information based on the fingerprints received.

Further scope of applicability of the present disclosure will become apparent from the detailed description given hereinafter. However, it should be understood that the detailed description and specific examples, while indicating preferred embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

Various embodiments of the present disclosure will be described herein below with reference to the figures wherein.

Figure 1:
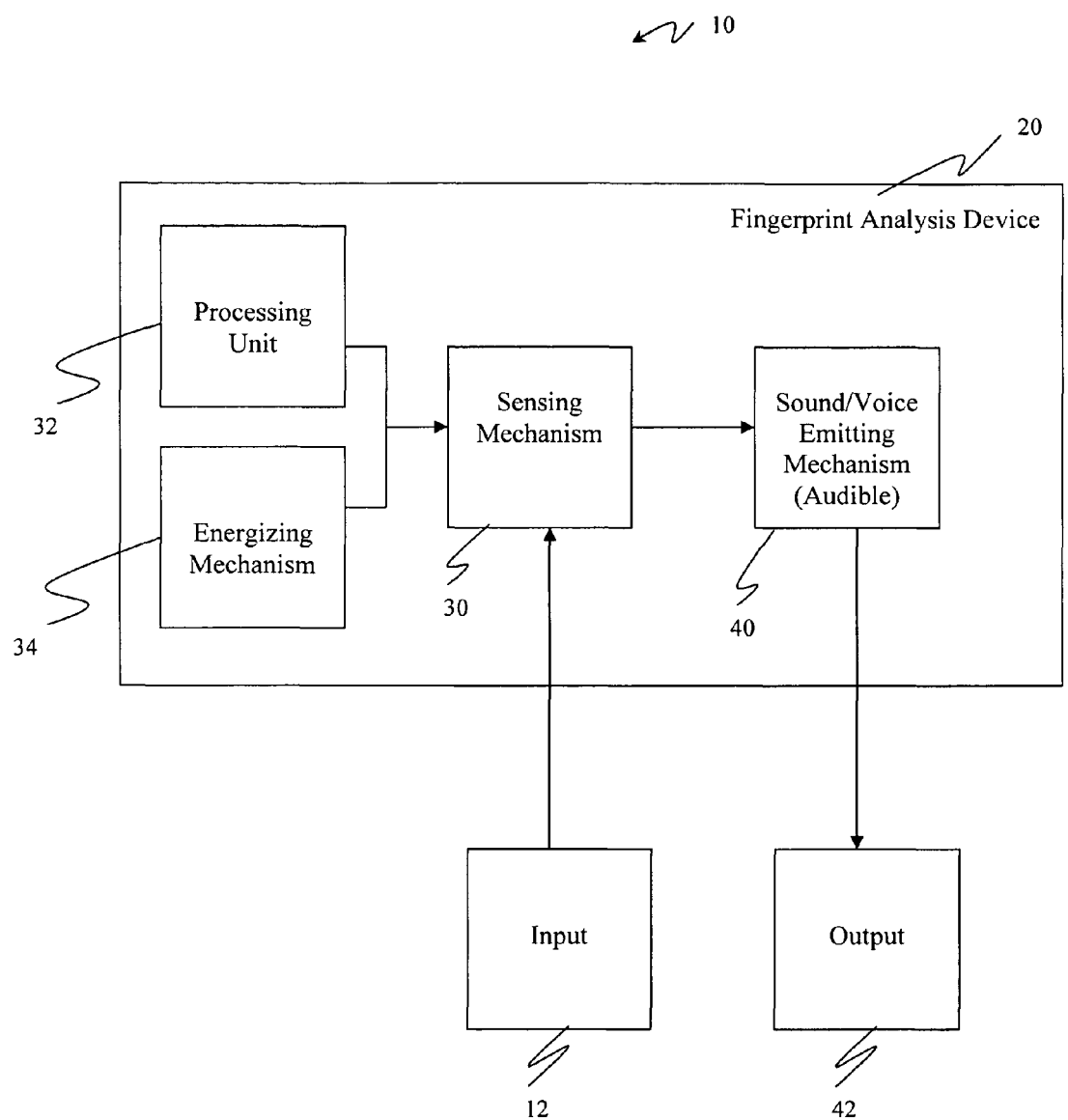
FIG. 1 is a system block diagram of a fingerprint analysis device emitting/conveying audible messages/information/data, in accordance with the present disclosure.

It is noted that the drawings of the present disclosure are not to scale. The drawings are intended to depict only typical embodiments of the present disclosure, and therefore should not be considered as limiting the scope of the present disclosure. In the drawings, like numbering represents like elements between the drawings.

DETAILED DESCRIPTION

Although the present disclosure will be described in terms of a specific embodiment, it will be readily apparent to those skilled in this art that various modifications, rearrangements and substitutions may be made without departing from the spirit of the present disclosure. The scope of the present disclosure is defined by the claims appended hereto.

For the purposes of promoting an understanding of the principles of the present disclosure, reference will now be made to the exemplary embodiments illustrated in the drawings, and specific language will be used to describe the same. It will nevertheless be understood that no limitation of the scope of the present disclosure is thereby intended. Any alterations and further modifications of the inventive features illustrated herein, and any additional applications of the principles of the present disclosure as illustrated herein, which would occur to one skilled in the relevant art and having possession of this disclosure, are to be considered within the scope of the present disclosure.

Reference throughout this specification to "one embodiment," "an embodiment," or similar language means that a particular feature, structure, or characteristic described in connection with the embodiment is included in at least one embodiment of the present disclosure. Thus, appearances of the phrases "one embodiment," "an embodiment," and similar language throughout this specification may, but do not necessarily, all refer to the same embodiment, different embodiments, or component parts of the same or different illustrated disclosure. Additionally, reference to the wording "an embodiment," or the like, for two or more features, elements, etc. does not mean that the features are related, dissimilar, the same, etc. The use of the term "an embodiment," or similar wording, is merely a convenient phrase to indicate optional features, which may or may not be part of the present disclosure as claimed. The independent embodiments are considered to be able to be combined in whole or in part one with another as the claims and/or art may direct, either directly or indirectly, implicitly or explicitly.

Moreover, the fact that the wording "an embodiment," or the like, does not appear at the beginning of every sentence in the specification, such as is the practice of some practitioners, is merely a convenience for the reader's clarity. However, it is the intention of this application to incorporate by reference the phrasing "an embodiment," and the like, at the beginning of every sentence herein where logically possible and appropriate.

Prior to describing the present disclosure in further detail, it will first be helpful to define various terms that will be used throughout the following discussion. For example:

In this application, the use of the singular includes the plural unless specifically stated otherwise. In this application, the use of "or" means "and/or" unless stated otherwise. Furthermore, the use of the term "including," as well as other forms, such as "includes" and "included," is not limiting. Also, terms such as "element" or "component" encompass both elements and components comprising one unit and elements and components that comprise more than one subunit unless specifically stated otherwise.

The term "grocery store" may be defined at least as a store established primarily for the retailing of food and/or a marketplace where groceries are sold and/or a food service establishment selling commercially prepackaged foods and/or beverages.

The term "supermarket" may be defined at least as a large self-service grocery store selling groceries and dairy products and household goods and/or a self-service store offering a wide variety of food and household merchandise, organized into departments. A "supermarket" may be larger in size and have a wider selection than a traditional grocery store and it may be smaller than a hypermarket or superstore. A "supermarket" may also be defined as a complete market offering food and nonfood items, including some partial service departments.

Terms that are synonymous with the term "grocery store" may be mom-and-pop store, bodega, convenience store, corner store, food mart, marketplace, market, food store, retail food store, supermarket, deli, delicatessen, chain store, department store, general store, drug store, discount store, and or any type of retail establishment that sells "items" or "products" as defined below.

The term "items" may at least refer to goods, products, merchandise, commodities, food, produce, drinks, beverages, articles, objects, materials, alcohol, cleaning products, medicine, electrical products, greeting cards, houseware products, personal hygiene products, novelties, etc. An item may be anything that is sold in a "grocery store" and/or "supermarket" as defined above, and any of the synonyms used to describe a "grocery store" and/or "supermarket." The term "item" may be used interchangeably with the term "product."

A "venue" may refer to any type of small or large, usually open structure for sports events and/or entertainment events, with tiered seating for spectators. A "venue" may be a stadium, ballpark, athletic field, bowl, coliseum, diamond, gymnasium, ring, rink, arena, park, theater, amphitheater, etc. A "sports venue" may also be any type of entertainment venue, where tickets are scanned in order for individuals to attend. A venue or arena may be any type of building or enclosure providing for entertainment and/or sports.

The term "analyze" may at least refer to determining the elements or essential features or functions or processes of one or more fingerprint recognition, collection, and analysis systems for computational processing. The term "analyze" may further refer to tracking data and/or collecting data and/or manipulating data and/or examining data and/or updating data on a real-time basis in an automatic manner and/or a selective manner and/or manual manner (continuously or periodically).

The term "storage" may at least refer to data storage. "Data storage" may refer to any article or material (e.g., a hard disk) from which information may be capable of being reproduced, with or without the aid of any other article or device. "Data storage" may refer to the holding of data in an electromagnetic form for access by a computer processor. Primary storage may be data in random access memory (RAM) and other "built-in" devices. Secondary storage may be data on hard disk, tapes, and other external devices. "Data storage" may also refer to the permanent holding place for digital data, until purposely erased. "Storage" implies a repository that retains its content without power. "Storage" mostly means magnetic disks, magnetic tapes and optical discs (CD, DVD, etc.). "Storage" may also refer to non-volatile memory chips such as flash, Read-Only memory (ROM) and/or Electrically Erasable Programmable Read-Only Memory (EEPROM).

The term "electronic device" may refer at least to one or more personal computers (PCs), a standalone printer, a standalone scanner, a mobile phone, an MP3 player, audio electronics, video electronics, GPS systems, televisions, recording and/or reproducing media (such as CDs, DVDs, camcorders, cameras, etc.) or any other type of consumer or non-consumer analog and/or digital electronics. Such consumer and/or non-consumer electronics may apply at least in any type of entertainment, communications, home, and/or office capacity. Thus, the term "electronic device" may refer to any type of electronics suitable for use with a circuit board and intended to be used by a plurality of individuals for a variety of purposes. The electronic device may be any type of computing and/or processing device.

The term "processing" may at least refer to determining the elements or essential features or functions or processes of one or more fingerprint recognition, collection, and analysis systems for computational processing. The term "process" may further refer to tracking data and/or collecting data and/or manipulating data and/or examining data and/or updating data on a real-time basis in an automatic manner and/or a selective manner and/or manual manner (continuously or periodically).

As used herein, the term "fingerprint" or "fingerprint image" may be used to refer to at least any type of detected fingerprint including but not limited to an image of all or part of one or more fingerprints (partial patterns), a rolled fingerprint, a flat stationary fingerprint, a palm print, and/or prints of multiple fingers.

The term "adhesive member" may refer at least to a gel, a viscous substance, a gelatin or gelatinous substance, a sticky substance, a gooey substance, a waxy substance, a gel tape and/or a bonding substance. The term "adhesive member" may refer to any type of substance that can receive a fingerprint and retain the fingerprint image for further processing. The term "adhesive member" may refer to a fingerprint scanner for receiving the fingerprint and retaining the fingerprint image for further processing. The "adhesive member" may be any type of device, apparatus, unit, module, configuration, mechanism, instrument, and/or structure for receiving the fingerprint and retaining the fingerprint image for further processing.

As used herein, the term "host processor" may be used to refer to any type of computer, processor(s), or logic which may receive and process fingerprint images detected by a remote fingerprint scanner. Such a processor may include software for performing one-to-one or one-to-many fingerprint matching and recognition or instead, for example in the case of a host processor used in a law enforcement vehicle, may be used to further transmit detected fingerprint image data to another processor for matching and recognition.

In one exemplary embodiment, the present disclosure proposes a system and method of incorporating a product/item at a grocery store and/or supermarket with a fingerprint analysis device for providing consumers with additional information related to the product/item. The present disclosure further proposes a system and method of incorporating a poster or display (or banner, sign, sheet, billboard, exhibit, sticker, paper advertisement, publication) at an entertainment venue with a fingerprint analysis device for providing consumers with additional information/data related to, for instance, the entertainment performed at the entertainment venue.

In the exemplary embodiments, the fingerprint recognition and analysis device is anticipated to be either a portable device or a non-portable device. The fingerprint analysis device is anticipated to be fixedly secured on a specific location of a product/item or poster/display or on any type of publication. A publication may be anything in written form.

In the exemplary embodiments, the fingerprint analysis device is not anticipated as a locking or unlocking mechanism/configuration. The fingerprint analysis device is not intended as a security device for locking/unlocking areas and/or vehicles and/or homes, etc. A locking/unlocking device function is not anticipated by the present embodiments. In contrast, the fingerprint analysis device is anticipated to provide or convey or transmit or dispatch information/data, such as advertisements and/or promotional information, to a subject or user or consumer or individual, when the user requests such information/data by touching or interacting with the fingerprint analysis device.

The present disclosure further proposes a fingerprint analysis device that scans or receives or interacts with the finger itself, not the product/item. In other words, it is an active detection system, since it requires a subject or user or consumer or individual to actively or voluntarily press or force or interact with the fingerprint analysis device.

In general, a conventional fingerprint scanner system has two basic jobs. It needs to get an image of a finger, and it needs to determine whether the pattern of ridges and valleys in this image matches the pattern of ridges and valleys in pre-scanned images. There are a number of different ways to get an image of an individual's finger. The most common methods today are optical scanning and capacitance scanning. Both types come up with the same sort of image, but they go about it in completely different ways. However, the embodiments of the present disclosure envision a novel fingerprint receiving apparatus/device/configuration/system that receives an impression of a fingerprint, retains that fingerprint impression, and instantly, automatically, on-the-spot, and in real-time analyzes the fingerprint impression to determine what audible message to output to a subject or consumer or individuals that inputs such fingerprint. In an alternative embodiment, it is contemplated that a non-audible message is provided to a user (e.g., a message transmitted to a cell phone or other portable or non-portable electronic device).

Most fingerprint scanner systems compare specific features of the fingerprint, generally known as minutiae. Typically, human and computer investigators concentrate on points where ridge lines end or where one ridge splits into two (bifurcations). Collectively, these and other distinctive features are sometimes called typica. The scanner system software uses highly complex algorithms to recognize and analyze these minutiae. The basic idea is to measure the relative positions of minutiae, in the same sort of way you might recognize a part of the sky by the relative positions of stars. Therefore, in general, the fingerprint analysis device may include an optical system that has a prism and a lens system, as known in the prior art (and discussed above with reference to optical scanners and capacitive scanners). However, the fingerprint analysis system of the present disclosure need not necessarily include an optical system. Instead, preferably, the fingerprint analysis system of the present disclosure includes an adhesive member that is capable of instantly, automatically, on-the-spot, and in real-time analyze the fingerprint and provide an audible output (or a non-audible output). A match is created between the chemical composition detected from the inputted fingerprint and one or more messages of a plurality of messages conveyed to the subject.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Embodiments will be described below while referencing the accompanying figures. The accompanying figures are merely examples and are not intended to limit the scope of the present disclosure.

With reference to FIG. 1, there is presented a system block diagram of a fingerprint analysis device, in accordance with the present disclosure.

The system block diagram 10 includes a fingerprint analysis device 20 having at least a sensing mechanism 30 and a sound emitting mechanism 40. The sensing mechanism 30 is in operative communication with a processing unit 32 and an energizing mechanism 34. An input 12 (e.g., a fingerprint) is received by the sensing mechanism 30 and an output 42 (e.g., an audible sound) is emitted by the sound emitting mechanism 40.

The sensing mechanism 30 may be any type of gelatin sensing mechanism for receiving and analyzing fingerprints. For example, the gelatin sensing mechanism may be a gel tape for collecting/gathering fingerprints. The sensing mechanism 30 may be constructed from one or more biomaterials and/or biochips and/or gel biochips and/or biosensors and/or bio-electronic sensors and/or microprocessors, all of which may or may not be constructed from flexible materials. Biochips, for example, may be employed for the electrical and optical detection of a plurality of molecules and/or biomolecules and/or organic compounds.

A chemical photograph or signature may be taken instantaneously, on-the-spot, in real-time, while the sensing mechanism 30 is positioned on a product/item or display, etc. The chemical photograph or signature or snapshot may automatically, on-the-spot, in real-time identify molecules that differentiate one person from another. For example, males may be detected based on greater amount of urea (one chemical of the urine), since males sweat more urea than women. The chemical photograph or signature or snapshot may include compounds of chemicals that may identify the age, gender, race, dietary preferences and/or lifestyle preferences of the subject or person or individual touching/pressing/contacting the sensing mechanism 30. The chemical photograph or signature or snapshot may also detect traces of items recently manipulated by a subject or person or individual. For example, in one example embodiment, such items may include gunpowder, smoke, drugs, explosives, and/or biological weapons. In other words, law enforcement personnel may be notified of such fingerprint identification and take the necessary steps to deter violent activities and/or potential terrorist attacks. Manners in which law enforcement may utilize the inventive concepts of the present disclosure will be described below.

Alternatively, the sensing mechanism 30 may support a plurality of scanner and/or sensor types, inclusive of, but not restricted to capacitive, thermal, optical, tactile, or ultrasonic sensors. The application of these sensors is determined by accuracy, user friendliness, and time for processing. The exemplary embodiments of the present disclosure may be implemented by using any of these types of scanners/sensors that may be converted to a gel-tape form to aid in the substantially instantaneous reception and analysis of one or more fingerprints.

The sound emitting mechanism 40 may be a voice output communication device and/or a speech generating device. The sound emitting mechanism 40 may emit one or more sounds (such as voice messages/verbal messages) that are pre-recorded and stored in a local or remote memory device (see FIG. 4). However, it is contemplated that the messages are not pre-recorded, but updated instantly, in real-time from an external source, such as a central hub (see FIG. 3).

The sound emitting mechanism 40 may include a plurality of messages related to gender, age, race, dietary information, lifestyle information or a combination thereof. For example, a first message may be conveyed to a black, 18-year old male and a second message may be conveyed to a black, 65-year old male. A different message may be conveyed to a 21-year old, white, female vegetarian than a 21-year old, white, female meat-eater. A database may provide for hundreds, if not thousands of messages, pertaining to myriad combinations of potential fingerprint inputs. Additionally, the fingerprint analysis device 20 may select a predetermined number of characteristics to analyze to convey a message.

Figure 8A:
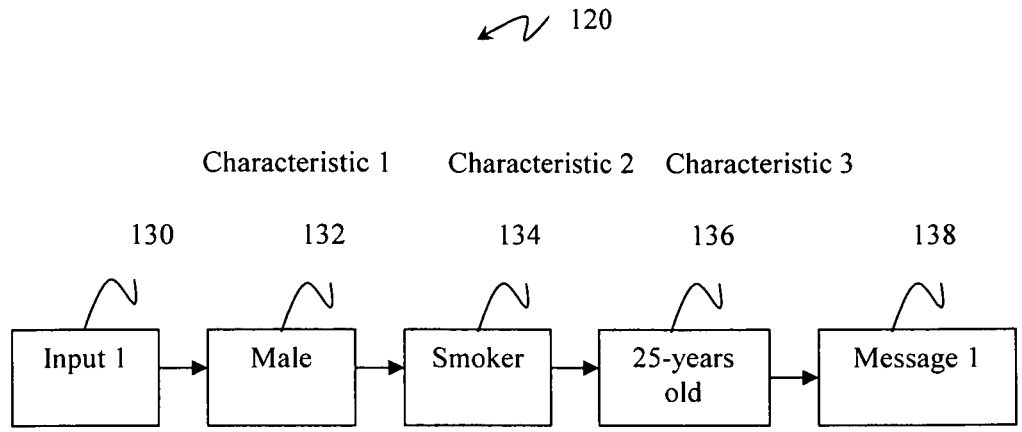
FIGS. 8A and 8B are block diagrams illustrating different output messages based on different characteristics analyzed by the fingerprint analysis device, in accordance with the present disclosure.
Figure 8B:
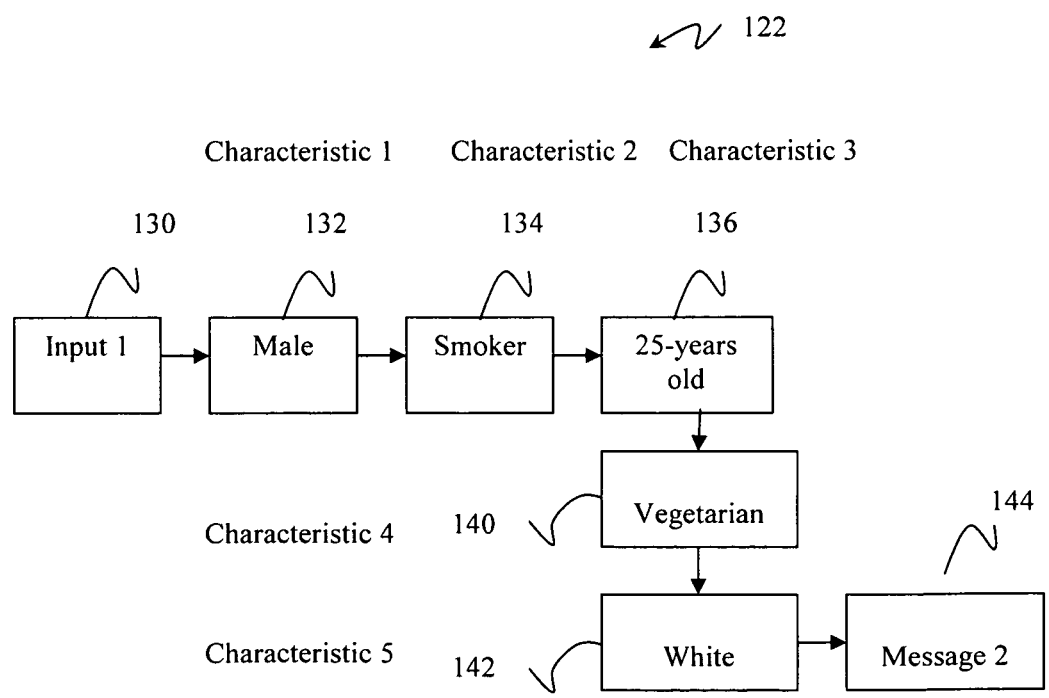

For example, 3 total characteristics may be used, 5 total characteristics may be use and/or 10 total characteristics may be used (see FIGS. 8A and 8B). One skilled in the art may contemplate using anywhere from 1 characteristic to hundreds, if not thousands, of characteristics to take into consideration before outputting a message based on a fingerprint.

Alternatively, the sound emitting mechanism 40 may be a removable medium, such as a CD, CD-ROM, DVD, flash disk, removable disk, thumb disk, or any other type of storage medium as defined herein. A person may insert the sound emitting mechanism 40 into the fingerprint analysis device 20 at predetermined time intervals to update the messages emitted/conveyed by the sound emitting mechanism 40. Alternatively, it is contemplated that the sound emitting mechanism 40 is updated remotely from an external source at predetermined time intervals, as discussed further below with reference to FIG. 3.

The output 42 is directly based on the inputted fingerprint. For example, if a male touches the sensing mechanism 30 and inputs a fingerprint, the output 42 may be of a first type. For instance, it emits information that may appeal more to a male. For example, if a female touches the sensing mechanism 30 and inputs a fingerprint, the output 42 may be of a second type. For instance, it emits information that may appeal more to a female. For instance, if the product/item incorporating the fingerprint analysis device 20 is cheese, a male may be more concerned with food to place it on, whereas a female may be more interested in nutritional information/content, such as caloric content, fat content, protein content, fiber, sugar, vitamins, etc. or vice versa. Therefore, the audible or voice messages emitted from the sound emitting mechanism 40 of the fingerprint analysis device 20 are different based on detection of gender. In other words, the emitted information is targeted information (i.e., targeted for a specific audience based on the chemical composition received from that person's fingerprint).

Alternatively, one person may touch/press/contact the sensing mechanism 30 and the sensing mechanism 30 may detect whether that person is a vegetarian or a meat eater. For example, vegetarians may have different amino-acid contents detected than a meat eater. For instance, as a result of such input, the sensing mechanism 30 emits information that may appeal more to a vegetarian, rather than a meat-eater. Therefore, the audible or voice messages emitted from the sound emitting mechanism 40 of the fingerprint analysis device 20 are different based on detection of a lifestyle characteristic. In other words, the emitted information is targeted information (i.e., targeted for a specific audience based on the chemical composition received from that person's fingerprint).

Alternatively, one person may touch/press/contact the sensing mechanism 30 positioned on a bottle of wine and the sensing mechanism 30 may detect that such person is a 35 year-old white male who enjoys red wine. The sound emitting mechanism 40 may include a plurality of pre-recorded messages that are activated based on such fingerprint photograph or signature received by the sensing mechanism 30. For example, the messages or sounds emitted may refer to other red wines sold by the same company or may refer to other white wines sold by the same company or may refer to how few calories are in the bottle of red wine compared to competitors or refer to any price or taste comparisons compared to competitors wines or may refer to food/meals that would nicely complement the red wine or may refer to consumer testimonials for such red wine or may refer to awards received for such red wine or may refer to cooking instructions for the red wine or may refer to where the grapes were picked from to make the red wine or may refer to the uniqueness of the grapes or soil, etc. Obviously, the audible messages emitted or voiced or transmitted or discharged may refer to a myriad of different possible messages for providing additional information or supplemental information or educational information or advertising information to a consumer or user or subject or person.

Targeted advertising may be a type of advertising whereby advertisements are placed so as to reach consumers based on various traits such as demographics, age, gender, race, dietary information, smoking behaviors, drinking behaviors and/or lifestyle information or a combination thereof. The advertising of the present example embodiments may be targeted interactive and targeted behavioral advertising. The advertising is interactive because a consumer is required to touch/press/contact or physically interactive with the sensing mechanism 30. The advertising is behavioral because a consumer's preferences are determined to emit/convey an appropriate message or text (whether audible or non-audible). In other words, sellers or manufacturers or producers of products/items may wish to convey specific messages to specific types of subjects or people. In order to accomplish such wish, targeted messages may be incorporated within the fingerprint analysis device 20 having a gel-type adhesive member (e.g., sensing mechanism 30) to convey targeted messages based on voluntary user input of a fingerprint. The messages are determined based on probabilities computed by advertisers or marketers or producers or manufacturers or any type of entity that sells, offers, licenses, promotes, etc. such products/items.

As a result, the system block diagram 10 may be used at a grocery store or supermarket, as defined herein. At the grocery store, each and every product/item may include such fingerprint analysis device 20. However, a fingerprint analysis device 20 may be included on the shelf of the product/item. The fingerprint analysis device 20 may be incorporated within or attached to a kiosk, as described below with reference to FIG. 10.

Of course, in an alternative embodiment, as described further below with reference to FIGS. 9 and 10, one skilled in the art may contemplate providing a display means incorporating the fingerprint analysis device 20, where such display means receives user input and displays messages or outputs instant coupons or discounts based on such input. The display means may be any type of electronic display, such as a flat panel display device, such as a liquid crystal display ("LCD"), a plasma display panel ("PDP") and an organic light emitting diode ("OLED"). Of course, one skilled in the art may contemplate using any type of display means/device/apparatus/configuration. Such display may be positioned in each aisle of a grocery store or may be centrally positioned as consumers walk into the grocery store. For example, the user may approach a kiosk (see FIG. 10) in a supermarket or grocery store that has a display means. The display means may enable the consumer to browse through and select a product/item of interest. When such product/item is selected, the user may input a fingerprint on the display means, which is instantly processed. Once processed, the kiosk may emit or transmit or convey a sound or voice providing the user with user-specific information. The kiosk may also provide the consumer with discounts and/or coupons related to the selection of such product/item and the message conveyed.

Alternatively, the fingerprint analysis device 20 need not be positioned or deposited on or attached to a product/item in a grocery store or supermarket. In accordance with the present disclosure, the fingerprint analysis device 20 may be positioned on an item that is not for sale. For example, the fingerprint analysis device 20 may be positioned on a poster or display or billboard or banner, sign, sheet, exhibit, sticker, paper advertisement, publication, etc. For instance, the fingerprint analysis device 20 may be positioned on a poster at a point-on-entry (POE) location.

For example, a POE location may be at sporting event venues or music venues (e.g., baseball games, basketball games, football games, hockey games, concerts, music festivals, etc.) For example, each attendee at a sporting event or concert must have a ticket. The ticket must be scanned for entry into the sporting event or concert. As the attendee enters the entertainment venue, several posters or paper displays or publications may be located throughout the venue. In accordance with the present disclosure, attendees may approach the several posters or paper displays or publications, each of which may include a fingerprint analysis device 20. The attendee may touch/press/contact the fingerprint analysis device 20 in order to enter a fingerprint. Based on such input, the fingerprint analysis device 20 analyzes the chemical photograph or signature of the fingerprint by identifying and analyzing, for example, the molecules and molecular compounds on the fingerprint. Based on the chemical analysis results, the poster or paper display or publication may emit or convey audible messages pertaining to the current entertainment event or to future entertainment events. For example, if a male inputs a fingerprint, one outputted message may refer to concession stands or to the lead singer's preferred guitar brand (if it is a music venue) or to the preferred baseball bat wood of a baseball player (if it is a sports venue). Of course, such posters or displays or publications or kiosks may be located throughout the entertainment venue.

Moreover, for example, a POE location may be a museum or art exhibit. For example, most attendees at an art exhibit walk around and preview the artwork. Adjacent each artwork there is usually placed a placard indicating the name of the artist, the name of the artwork, the year it was completed, a short description of the artwork, etc. In accordance with the present disclosure, it is contemplated that a fingerprint analysis device 20 is positioned next to each artwork in an exhibit or museum or similar establishment. For example, if one enters a Pablo Picasso exhibit and looks at a specific Picasso painting, that person may want to learn more details related to such painting. If a male inputs a fingerprint image on the fingerprint analysis device 20, a message may be emitted indicating that this painting was completed during Picasso's Blue Period, when he was depressed, thus explaining the somber mood of the painting. Another message might refer to bars and restaurants Picasso frequented in Barcelona. Another message might refer to other "extracurricular" activities he enjoyed in Barcelona. If a female inputs a fingerprint image on the fingerprint analysis device 20, a message may be emitted indicating other Artists' Picasso admired. Another message might indicate that his birthday is Oct. 25, 1881. Another message may indicate other paintings from a similar era and where they are located throughout the world. Another message may include information related to Picasso's early childhood. Another message may refer to discounts at the museum gift shop related to Picasso posters or prints. Of course, one skilled in the art may contemplate a myriad of different messages that may be displayed or emitted or transmitted or conveyed to a man or a woman. One skilled in the art may contemplate a myriad of different messages to be displayed or emitted or transmitted or conveyed based on gender, race, age or other preferences/characteristics or a combinations thereof.

Moreover, in yet another non-limiting example, a 5-year old child may touch the fingerprint analysis device 20 attached to a Keebler™ cookie box. The sound emitting mechanism 30 of the fingerprint analysis device 20 may emit a message informing the child that the Keebler™ elves (e.g., Ernie and Elwood) absolutely love this type of cookies. Another message may refer to all the names of the elves that helped make the cookies or may refer to the amount of chocolate chips in each cookie or may refer to sports that each elf likes to play or may encourage the child to have milk with the cookies or may refer to the amount of cookies the child should have in one sitting or may refer to other characters that enjoy such cookies (e.g., SpongeBob™, Bob the Builder™, etc.) or may refer to the child to go to the Keebler™ website for new fun games to be played, etc. Once again, a myriad of message may be contemplated to be conveyed in such non-limiting example. Additionally, the parent or relative who is accompanying the 5-year old child may touch the fingerprint analysis device 20 attached to a Keebler™ cookie box. The sound emitting mechanism 30 of the fingerprint analysis device 20 may emit a message informing the relative or parent of the nutritional content, the fat content, how the fat content compares to a competitor's cookie fat content, other popular cookies made by the same company, etc. As a result, different messages may be conveyed based on the inputted fingerprints in order to achieve targeted outputs.

Moreover, in yet another non-limiting example, a person may visit a movie theater. Many movie theaters already include movie ticket kiosks for purchasing tickets to movies playing at such theater. All the movies are presented to a user on a display screen. It is contemplated, that in addition to the other information presented, that a fingerprint analysis device 20 may be incorporated with such movie ticket kiosk, to provide a user with a determination of whether such person enjoys such movie. For example, the user may enter a fingerprint on the display of the movie ticket kiosk, and the fingerprint analysis device 20 may detect the chemical composition of the fingerprint to determine the characteristics of the user. The characteristics of the user may be used to allow the sound emitting mechanism 30 to convey a message to the user. If the movie Rambo™ is selected by a white, 50-year old woman, with a selective diet, non-smoker, etc., the sound emitting mechanism 30 of the fingerprint analysis device 20 incorporated within or on the movie ticket kiosk may inform the woman that such movie appeals more to 21-40 year old males and that statistics collected from the past 2 weeks reveal that 90% of the patrons who watched this movie in this theater were males in the 21-40 year old range. As such, the woman may decide to view another movie. Of course, the message conveyed may pertain to positive movie critiques by popular movie critics or other celebrities or the message conveyed may pertain to other movies starring the lead actor or may convey how much money the selected movie has made to date or may refer to amounts of money contributed to charity by the actors/directors/producers of the movie or may refer to preferred charities of the actors or may refer to environmentally-conscious products used to make the movie or may refer to making donations to a natural disaster (e.g., Haiti disaster), etc. A plurality of different message may be envisioned by advertising and/or marketing companies/entities that pertain to any cause, economic or non-economic to influence the person who inputted the fingerprint.

Moreover, in yet another non-limiting example, trading cards (e.g., baseball cards, basketball cards, football cards, etc.) may include the fingerprint analysis device 20. A user contacting the sensing mechanism 30 of the fingerprint analysis device 20 may receive a plurality of different messages. For example, if a 10-year old child activates the fingerprint analysis device 20 on the baseball card, the message may relate to the player's stats or the player's favorite foods or the player's favorite cities or the player's involvement with the community or encouraging messages about school or encouraging messages about physical activity or messages related to obesity and how to fight it or promotional items or a preferred baseball item (e.g., wooden bat, glove, sunglasses, etc.), etc. Furthermore, if a 40-year old activates the fingerprint analysis device 20 on the baseball card, the message may relate to charities promoted by the player or promoting a baseball fantasy league or promoting a baseball fantasy camp or favorite beer of the player or any type of advertisement or promotional material or educational material, etc. Once again, a plurality of different message may be envisioned by advertising and/or marketing companies/entities that pertain to any cause, economic or non-economic to influence the person who inputted the fingerprint.

Moreover, in yet another non-limiting example, a personal computer (PC) may incorporate or be associated with or be in operative communication with the fingerprint analysis device 20. Of course any type of electronic device, as defined herein, may incorporate or be associated with or be in operative communication with the fingerprint analysis device 20, including, but not limited to, MP3 players and cell phones. For example, a user may access Google™ via the Internet on the PC. A user may type the term "baseball" in Google™. A user may input a fingerprint via the fingerprint analysis device 20 and Google™ may provide advertisements based on the inputted fingerprint. For example, the advertisements will relate to baseball, but they will be gender-specific or age-specific or race-specific, etc. Thus, the chemical composition of the fingerprint detected may enable advertisers to provide for better and more efficient target advertising. If the user is only 7-years old, the advertisements displayed based on the search term "baseball" may be quite different than the advertisements displayed for a 55-year old who enters the term "baseball" in Google™. Thus, the advertisers might want to target the 7-year old with ads related to bubble gum or baseball cards or baseball caps, etc., whereas the advertisers might want to target the 55-year old with signed memorabilia, fantasy camps, beer, bars close to ballparks, etc.

Additionally, fingerprint-specific searches may be enabled via Google™ or another search engines (e.g., Bing™). For example, a person may desire to purchase a digital camera. A user may first enter a fingerprint via the fingerprint analysis device 20 and then type the term "digital camera" in Google™. Google™ may return results based on the term "digital camera," as well as the chemical composition of the fingerprint inputted via the fingerprint analysis device 20. Thus, search results of search engines may be modified to provide for more specific or targeted advertising output based on gender, age, race, lifestyle determinations/characteristics provided substantially instantaneously, in real-time. A 25-year old black female may desire a totally different digital camera than a 70-year old white male. As a result, it would be in the advertisers best interest to use a mechanism, such as the one proposed herein, whereby chemical compositions of fingerprints provide advertisers with more accurate information related to the user, in order to provide products/items that will have a higher probability of enticing a specific group of people.

Of course, these are only non-limiting examples of where such fingerprint analysis device 20 may be used. It is contemplated that such fingerprint analysis device 20 may be used in any type of industry for any type of application where a user voluntarily inputs a fingerprint and the fingerprint analysis device 20 outputs predetermined or updated messages in audible format (or non-audible format, to an electronic device, see FIG. 9). The chemical analysis of the fingerprint occurs substantially instantaneously with the input or within a short predetermined time period of the input. A match is determined between the chemical composition of the inputted fingerprint and the pre-recorded messages (or eventual updated messages) to determine a probability of which message or messages would be most appropriate based on the inputted fingerprint and subsequent chemical analysis of the fingerprint.

Figure 2:
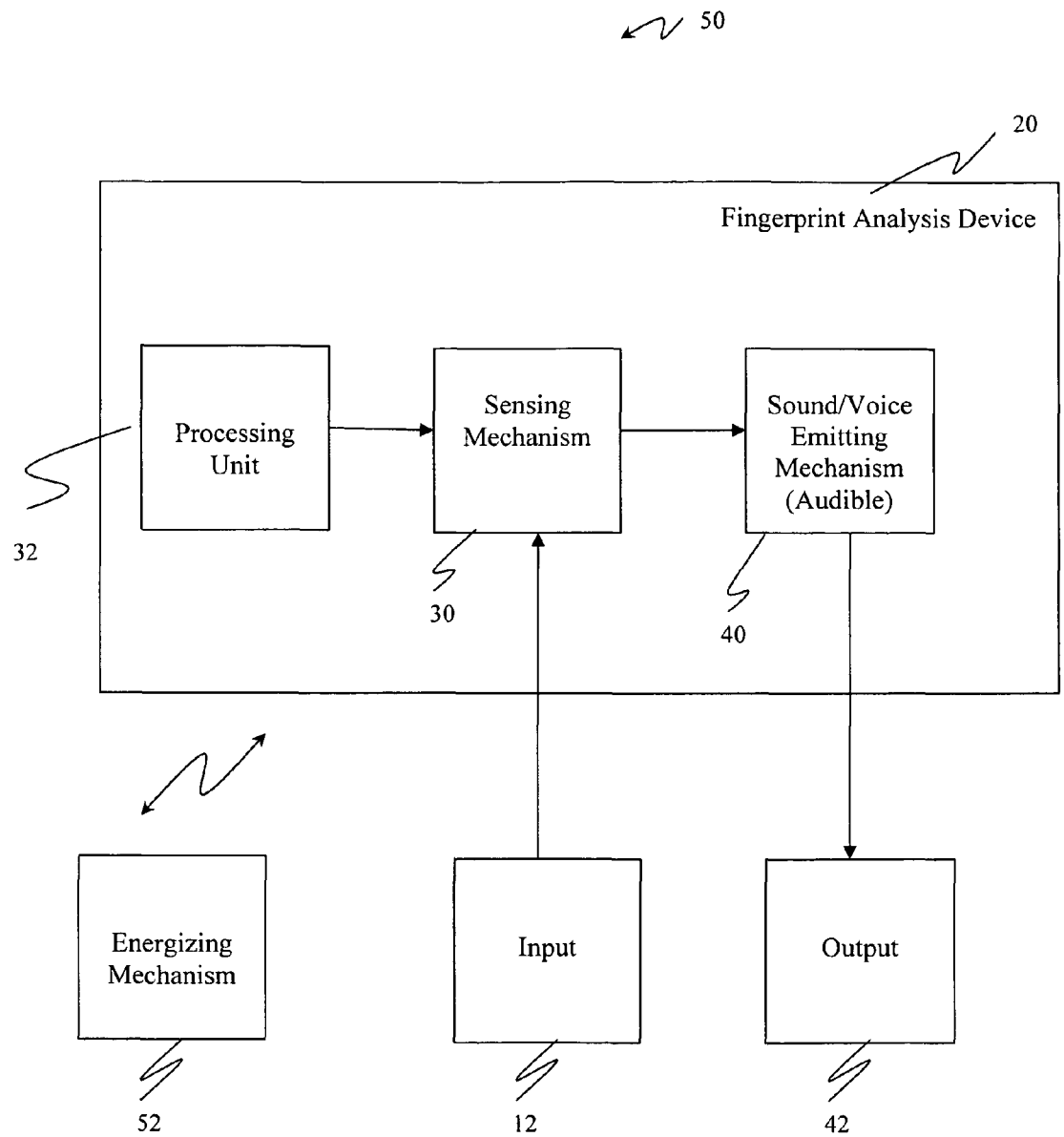
FIG. 2 is a system block diagram of a fingerprint analysis device operatively cooperating with a remotely located energizing mechanism, in accordance with the present disclosure.

With reference to FIG. 2, there is presented a system block diagram of a fingerprint analysis device operatively cooperating with a remotely located energizing mechanism, in accordance with the present disclosure.

The system block diagram 50 is similar to the system block diagram 10 of FIG. 1. Therefore, similar elements to FIG. 1 will not be described in detail. In contrast to FIG. 1, FIG. 2 includes an energizing mechanism 52 that is remotely located with respect to the fingerprint analysis device 20.

The energizing mechanism 52 may be a battery, a solar panel, or any other type of mechanism for providing power to the fingerprint analysis device 20. The energizing mechanism 52 may be a wired mechanism or a wireless mechanism. The energizing mechanism 52 may be located in the vicinity of the fingerprint analysis device 20 or may be located within a distant predetermined radius of the fingerprint analysis device 20.

Figure 3:
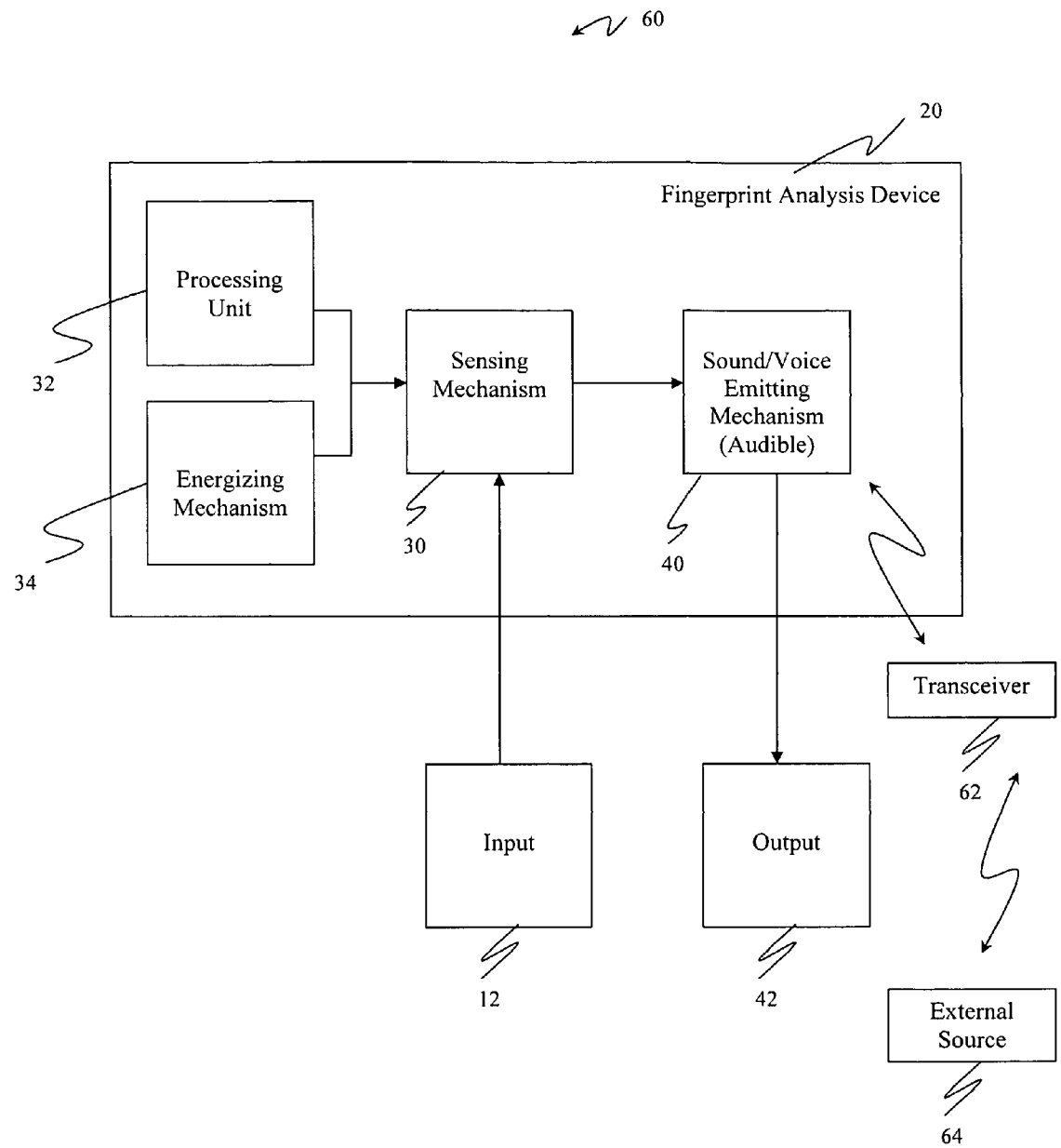
FIG. 3 is a system block diagram of a fingerprint analysis device operatively cooperating with a transceiver, which in turn cooperates with an external source, in accordance with the present disclosure.

With reference to FIG. 3, there is presented a system block diagram of a fingerprint analysis device operatively cooperating with a transceiver, which in turn cooperates with an external source, in accordance with the present disclosure.

The system block diagram 60 is similar to the system block diagram 10 of FIG. 1 and the system block diagram 50 of FIG. 2. Therefore, similar elements to FIGS. 1 and 2 will not be described in detail. In contrast to FIGS. 1 and 2, FIG. 3 includes a transceiver 62 and an external source 64.

The transceiver 62 may be located within the fingerprint analysis device 20, may be attached to the fingerprint analysis device 20 or may be located in a remote location with respect to the fingerprint analysis device 20. The transceiver 62 may be used to receive one or more updated sounds from the external source 64 and to transmit feedback information to the external source 64. The information may be transmitted or received either in a wired configuration or in a wireless configuration. The transceiver 62 may receive a plurality of different information/data from the external source 64. The information may be related to updated messages to convey to users inputting fingerprints. The information may be transmitted automatically in predetermined time intervals (e.g., daily, weekly, monthly, etc.) or may be transmitted based on demand (or a prompt) from the grocery store or entertainment venue. The external source 64 may be a computer or electronic device that is continuously updated with messages by the manufacturers or sellers or producers of the product/item or display or poster or publication. The external source 64 may be prompted to transmit the updated or new information/messages or may do so in an automatic manner.

Additionally, based on the information received, the information may be recorded and categorized into historical or statistical data in order to allow the manipulators (e.g., advertisers or marketers or sellers or producers or manufacturers, etc.) of the external source 64 to determine which messages to send to which locale based on the feedback information. For example, a store in one location may have more white male clientele between the ages of 21-45, whereas a store in another locale may have more white female clientele between the ages of 40-65. As a result, the external source 64 may be calibrated to send more direct targeted output based on such historical or statistical determinations. Once again, a determination is made as to what the characteristics of the subject are. Such characteristics may include at least age, gender, race, dietary information, and/or lifestyle information, or a combination thereof, and targeted messages/output based on such collected data may be conveyed substantially instantaneously, in real-time.

Figure 4:
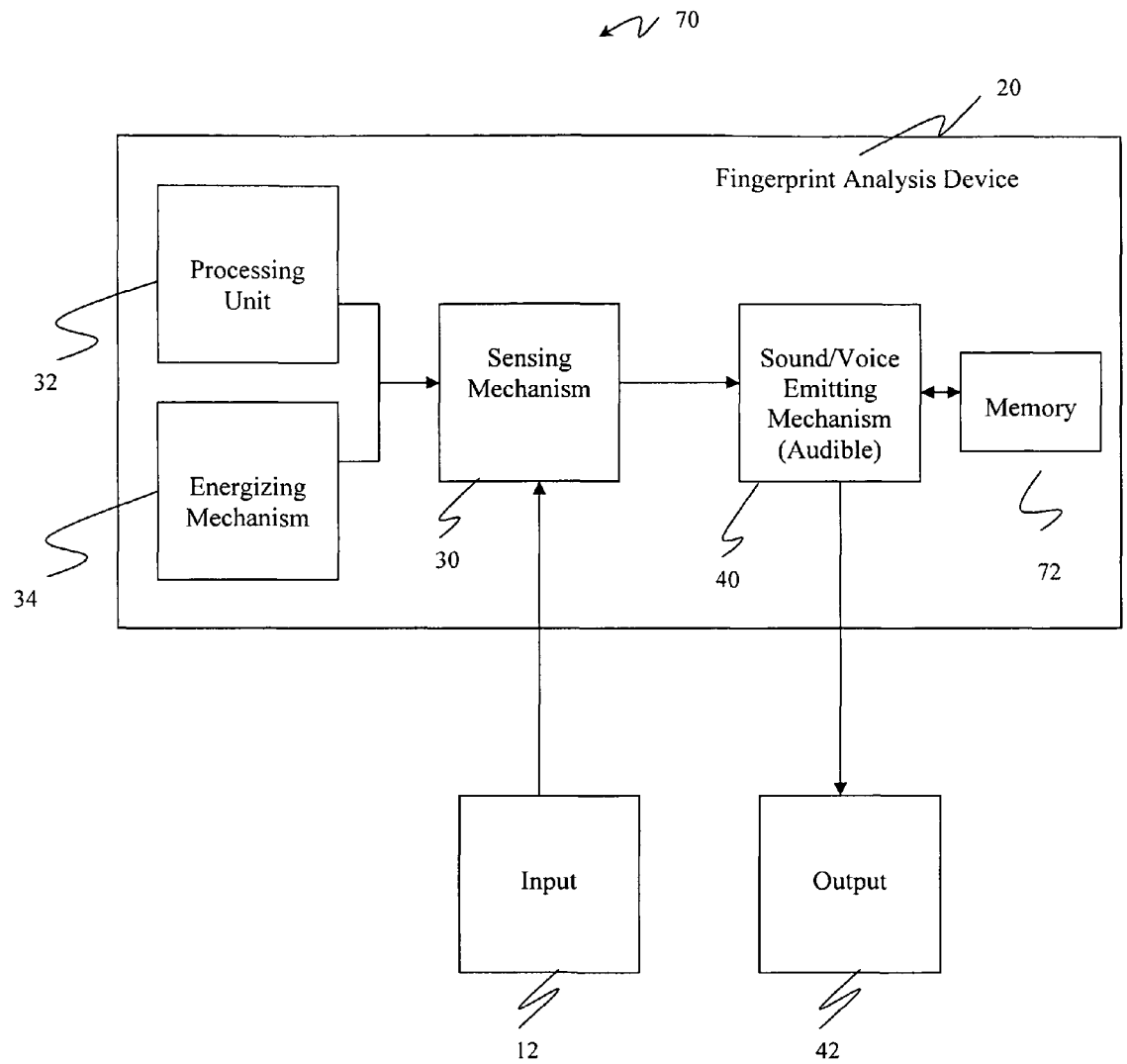
FIG. 4 is a system block diagram of a fingerprint analysis device where the sound emitting mechanism operatively cooperates with a memory unit, in accordance with the present disclosure.

With reference to FIG. 4, there is presented a system block diagram of a fingerprint analysis device where the sound emitting mechanism operatively cooperates with a memory unit, in accordance with the present disclosure.

The system block diagram 70 is similar to the system block diagram 60 of FIG. 3. Therefore, similar elements to FIG. 3 will not be described in detail. In contrast to FIG. 3, FIG. 4 includes a memory element 72.

Memory element 72 may be any type of data storage system, as defined herein. Memory element 72 may be a storage module or a storage unit. The memory 72 may be one or more databases. The memory 72 may include a plurality of records. The memory 72 may be centralized (as in a fingerprint repository) or distributed (as in a plurality of fingerprint scanners). The records may be stored in the form of a table, list, or other data structure (or combination of data structures) known to those of skill in the art. Each of the records may include an identifier field, which stores a unique identifier associated with a person of interest. Thus, each of the records in the memory 72 is associated with a message directly associated with or correlated to one or more characteristics of the input fingerprint.

Figure 5:
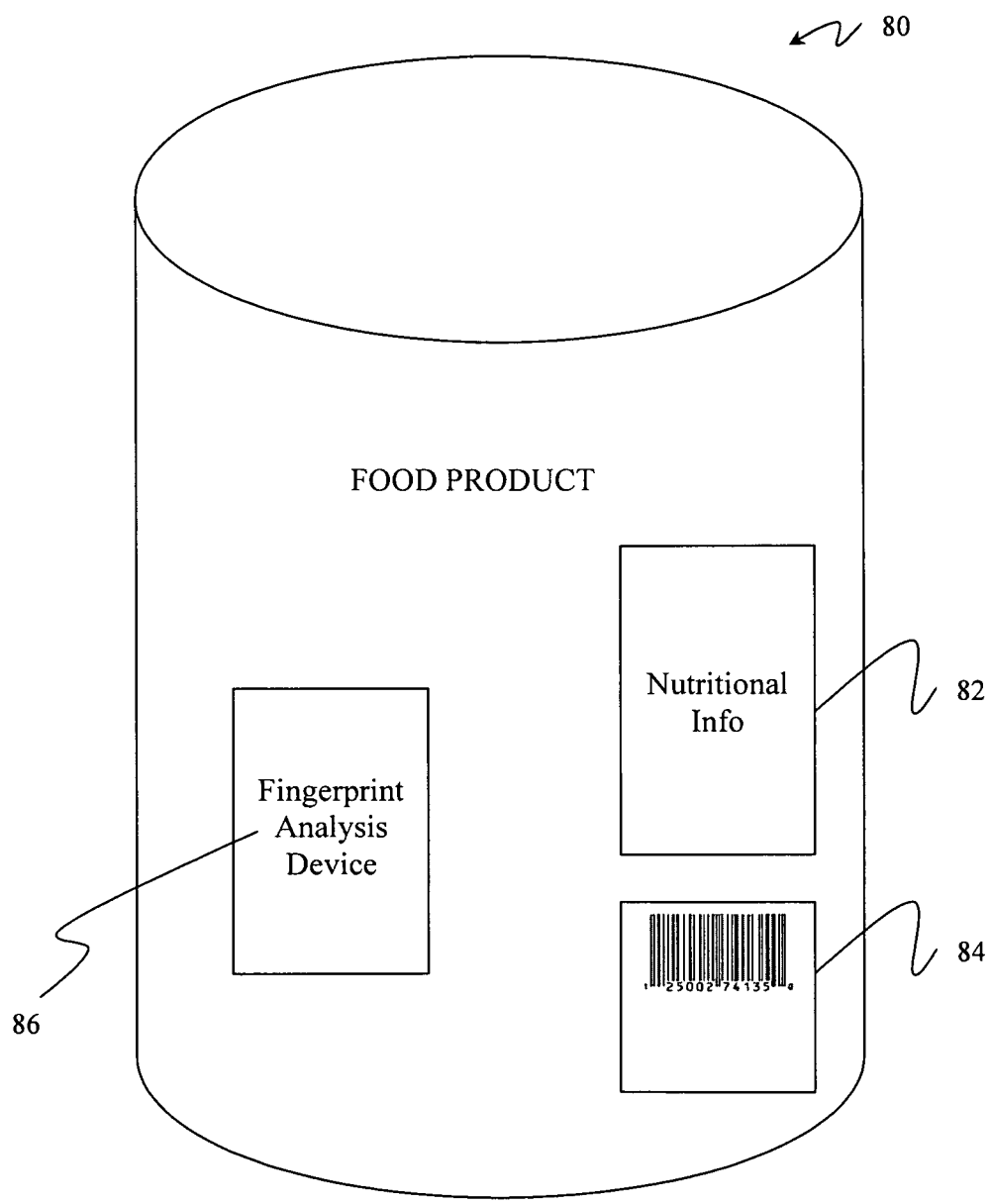
FIG. 5 is a perspective view of a food item having a barcode and a fingerprint analysis device, in accordance with the present disclosure.

With reference to FIG. 5, there is presented a perspective view of a food item having a barcode and a fingerprint analysis device, in accordance with the present disclosure.

The food product 80 usually includes at least a nutritional information label 82 and a bar code 84. Additionally, in accordance with the example embodiments of the present disclosure, the food product 80 may also include a fingerprint analysis device 86. The fingerprint analysis device 86 may be positioned on any portion of the food item (top, bottom side). Of course, this is only a non-limiting example. It is contemplated that the fingerprint analysis device 86 may be positioned or attached to or in operable communication with a plurality of items/products in any type of grocery store or entertainment venue, as the terms are defined herein.

Alternatively, it is also contemplated that the barcode 84 is incorporated with or embedded into the fingerprint analysis device 86. In other words, such elements 84, 86 may be combined into one unit and operate concurrently, instead of independently as described herein.

Figure 6:
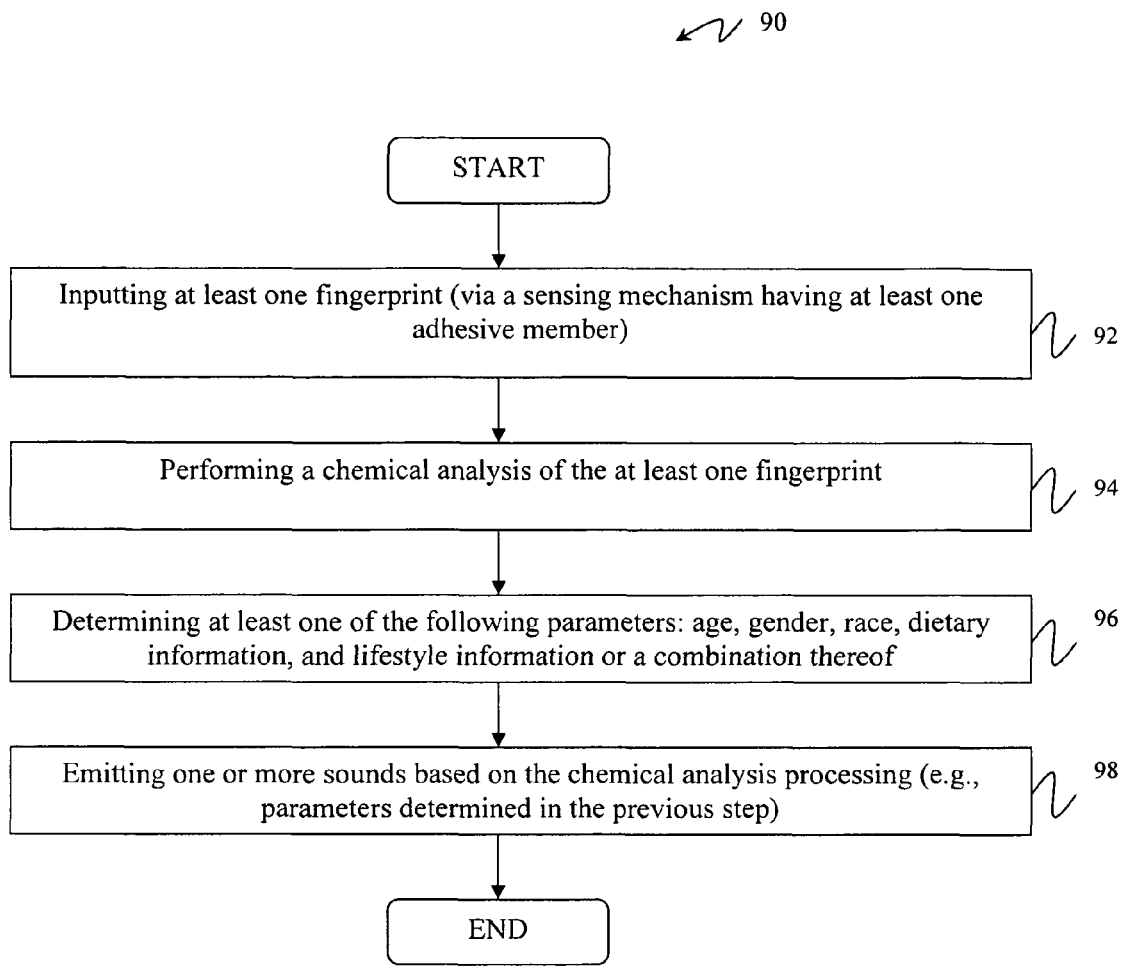
FIG. 6 is a flowchart illustrating how a fingerprint analysis device collects, transmits, and analyzes fingerprints, in accordance with the present disclosure.

With reference to FIG. 6, there is presented a flowchart illustrating how a fingerprint analysis device collects, transmits, and analyzes fingerprints, in accordance with the present disclosure.

The flowchart 90 includes the following steps. In step 92, at least one fingerprint is inputted via a sensing mechanism having at least one adhesive member. In step 94, a chemical analysis of the at least one fingerprint is performed. In step 96, at least one of the following parameters: age, gender, race, dietary information, and lifestyle information or a combination thereof is determined by the chemical analysis. In step 98, one or more sounds based on the chemical analysis processing (e.g., parameters determined in the previous step) is emitted. The process then ends for the first cycle or first iteration. However, the process may be a continuous iterative process. In other words, the steps of the process may repeat for a number cycles or iterations, where the scanning, transmitting, receiving, and analyzing steps are constantly repeated.

Figure 7:
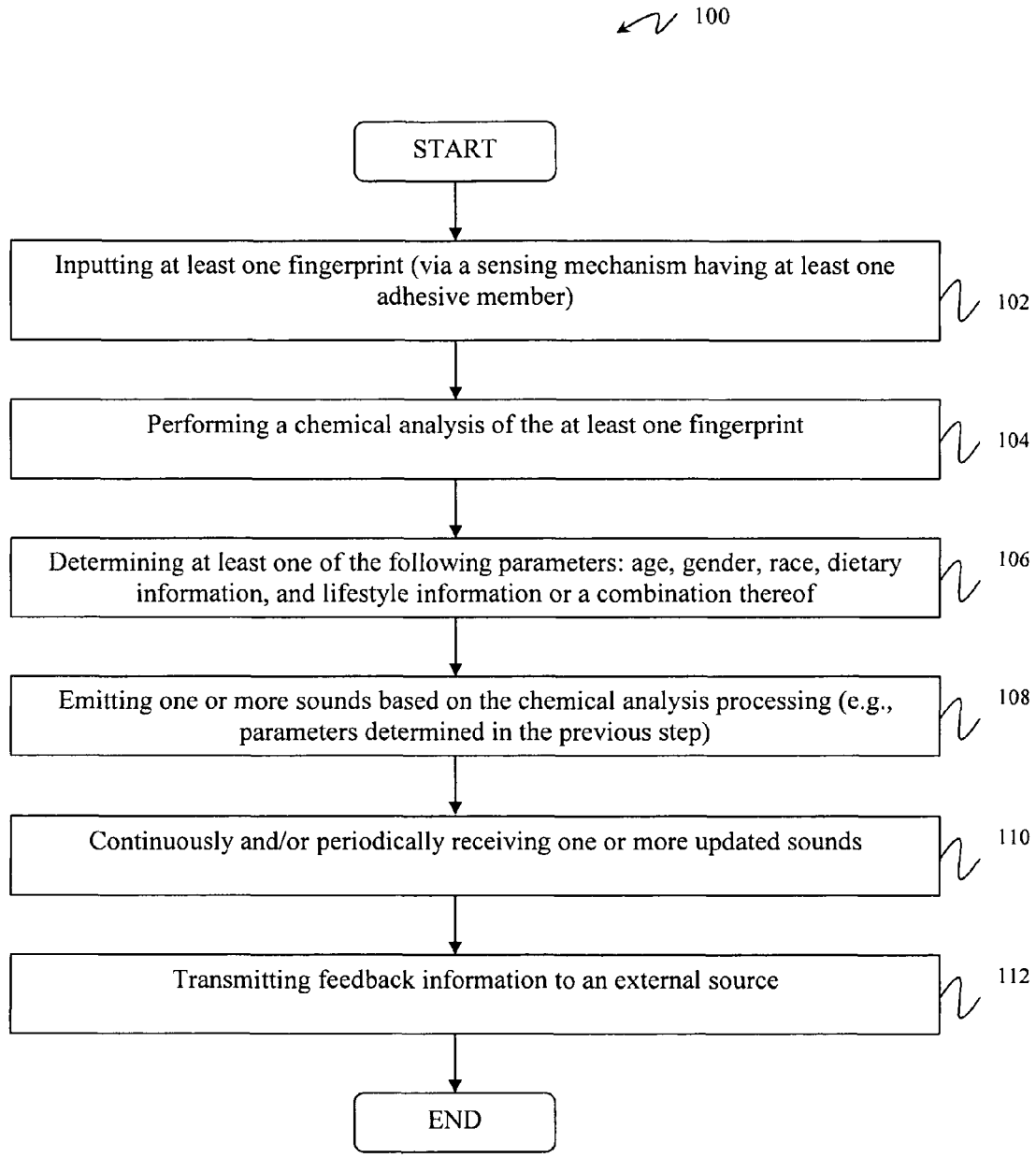
FIG. 7 is a flowchart illustrating how a fingerprint analysis device collects, transmits, and analyzes fingerprints, including acknowledging updated information and feedback features, in accordance with the present disclosure.

With reference to FIG. 7, there is presented a flowchart illustrating how a fingerprint analysis device collects, transmits, and analyzes fingerprints, including updating and feedback features, in accordance with the present disclosure.

The flowchart 100 includes the following steps. In step 102, at least one fingerprint is inputted via a sensing mechanism having at least one adhesive member. In step 104, a chemical analysis of the at least one fingerprint is performed. In step 106, at least one of the following parameters: age, gender, race, dietary information, and lifestyle information or a combination thereof is determined by the chemical analysis. In step 108, one or more sounds based on the chemical analysis processing (e.g., parameters determined in the previous step) is emitted. In step 110, one or more updated sounds are continuously and/or periodically provided to the fingerprint analysis device. In step 112, feedback information is transmitted to an external source. The process then ends for the first cycle or first iteration. However, the process may be a continuous iterative process. In other words, the steps of the process may repeat for a number cycles or iterations, where the scanning, transmitting, receiving, and analyzing steps are constantly repeated.

With reference to FIGS. 8A and 8B, block diagrams illustrating different output messages based on different characteristics analyzed by the fingerprint analysis device, in accordance with the present disclosure are presented.

The first sequence 120 of FIG. 8A includes a first input 130. The first input 130 is a fingerprint voluntarily inputted by a consumer to activate the fingerprint analysis devices, as described herein. In this example, the sensing mechanism(s) of the fingerprint analysis devices may be programmed to detect 3 main characteristics of the consumer based on the inputted fingerprint. For example, first characteristic 132 may relate to the gender (e.g., male), the second characteristic 134 may relate to a lifestyle choice (e.g., smoker), and the third characteristic 136 may relate to age (e.g., 25 years old). Based on those 3 detected characteristics, the fingerprint analysis device may output a first message 138.

The second sequence 122 of FIG. 8B includes the first input 130. The first input 130 is a fingerprint voluntarily inputted by a consumer to activate the fingerprint analysis devices, as described herein. In this example, the sensing mechanism of the fingerprint analysis devices may be programmed to detect 5 main characteristics of the consumer based on the inputted fingerprint. For example, first characteristic 132 may relate to the gender (e.g., male), the second characteristic 134 may relate to a lifestyle choice (e.g., smoker), the third characteristic 136 may relate to age (e.g., 25 years old), the fourth characteristic 140 may relate to an additional lifestyle choice (e.g., vegetarian), and the fifth characteristic 142 may relate to race (e.g., white). Based on those 5 detected characteristics, the fingerprint analysis device may output a second message 144. The second message 144 may the same or may be different than the first message 138 of FIG. 8A. This determination may be based on the amount of messages in the memory or database (local or remote) or the sophistication in the software developed to decide on what message of the plurality of messages to output.

Figure 9:
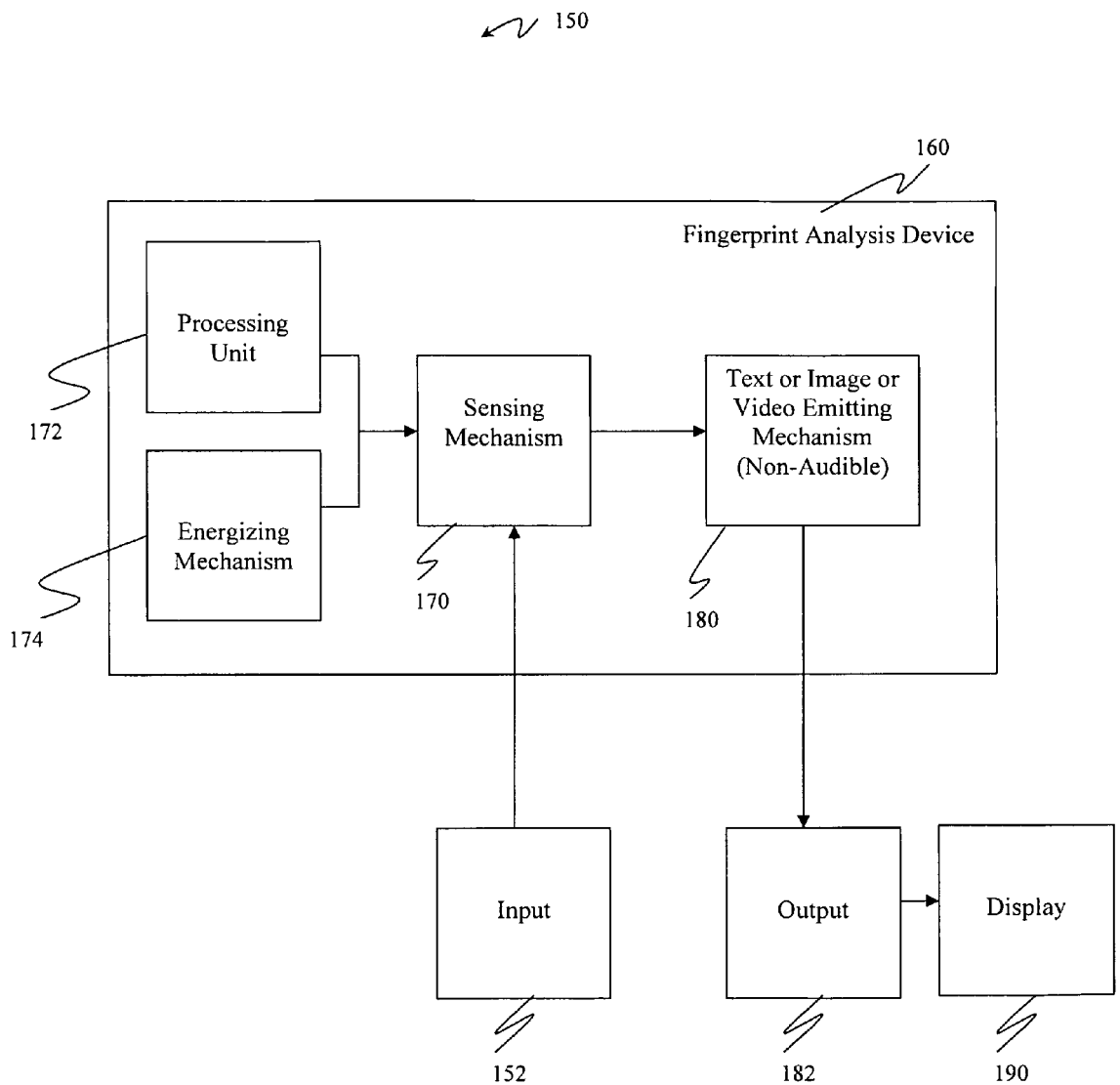
FIG. 9 is a system block diagram of a fingerprint analysis device emitting non-audible messages/information/data as an output to an electronic device, in accordance with the present disclosure.

With reference to FIG. 9, a system block diagram of a fingerprint analysis device emitting non-audible messages/information/data as an output to an electronic device, in accordance with the present disclosure is presented.

The system block diagram 150 includes a fingerprint analysis device 160 having at least a sensing mechanism 170 and a text or image or video emitting mechanism 180. The text or image or video emitting mechanism 180 is in operative communication with a processing unit 172 and an energizing mechanism 174. An input 152 (e.g., a fingerprint) is received by the text or image or video emitting mechanism 180 and an output 182 (e.g., a non-audible sound or a combination of audio/video messaging) is emitted by the text or image or video emitting mechanism 180. Additionally, the system block diagram 150 includes a display 190 for displaying the outputted text/images/video from the text or image or video emitting mechanism 180.

For example, the text or image or video emitting mechanism 180 may emit information/data related to a product/item at a grocery store to a consumer's cell phone or other portable or non-portable electronic device. The additional information may relate to testimonials of other users of the product/item, may relate to cooking recipes, may relate to instant coupons or discounts, may relate to further advertising information, etc. Such data may be instantly and promptly displayed on the display 190 of the portable or non-portable electronic device of the consumer who inputted a fingerprint via the fingerprint analysis device.

Figure 10:
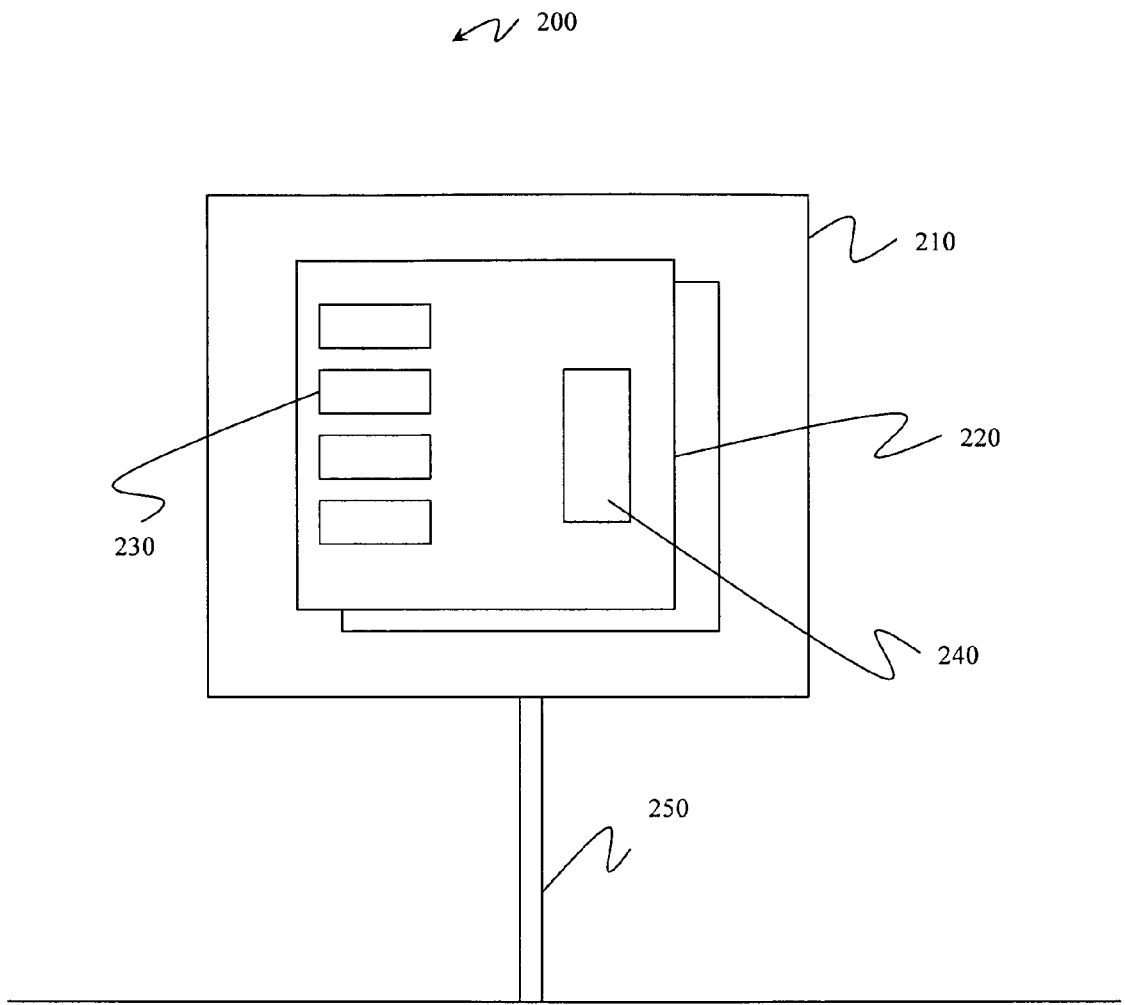
FIG. 10 is a standalone unit, such as a kiosk, including a display means incorporating at least one of the fingerprint analysis devices of FIGS. 1-5 and 9, in accordance with the present disclosure.

With reference to FIG. 10, a standalone unit, such as a kiosk, including a display means incorporating at least one of the fingerprint analysis devices of FIGS. 1-5 and 9, in accordance with the present disclosure is presented.

In an alternative embodiment of the present disclosure, a standalone kiosk 200 may be envisioned. The kiosk 200 may be located, for example, in a grocery store. The kiosk 200 may include a housing 210 and a display 220. The display 220 may present a fingerprint analysis device 240 and one or more products/items 230. The kiosk 200 may be supported by a stand 250. A consumer may approach the kiosk 200 and input a fingerprint via the fingerprint analysis device 240. The user may then browse through the one or more products/items 230 and select desired products/items 230. As the user selects such products/items 230, the kiosk 200 may provide additional information to the user based on the selections. The kiosk 200 may also dispense coupons or discounts based on the fingerprint inputted and the characteristics determined from the fingerprint analysis device 240.

It is contemplated that a series of kiosks 200 are presented at a grocery store or entertainment venue. It is contemplated that each aisle in a grocery store may include a kiosk 200, the kiosk 200 storing information related to products/items of that aisle. One skilled in the art may contemplate a number of different kiosk configurations to aid consumers in receiving additional information based on fingerprint inputs, fingerprint analysis, and fingerprint characteristics.

Preferably, an audible output is emitted by the fingerprint analysis devices 10, 50, 60, and 70. However, it is contemplated that one skilled in the art may design the fingerprint analysis systems 10, 50, 60, and 70 to emit non-audible signals (see FIG. 9). For example, signals may be transmitted to a cell phone or laptop, which may display text outputs or visual outputs. The visual outputs may be additional discounts and/or instant coupons that are immediately applicable. The text outputs may relate to additional information about the item/product, recalls on similar products or competitors products, comparison with competitors products/items.

Alternatively, the fingerprint analysis device may emit or convey both audible and non-audible messages. For example, the manufacturer may determine whether audible or non-audible messages are emitted or conveyed, separately or simultaneously. However, it is contemplated that a user may be permitted to select either an audible or non-audible message directly from the fingerprint analysis systems 10, 50, 60, 70, 150. A separate selection mechanism may be positioned on such fingerprint analysis systems.

Alternatively, a plurality of adhesive members may be provided. In other words, an adhesive member may be composed of a plurality of adhesive members in a serial or parallel configuration. The fingerprint analysis device may include a plurality of scanners and/or sensors and/or adhesive members for scanning a fingerprint from a plurality of different angles. As a result, multiple images may be collected from a single fingerprint on an item. Additionally a sensor/scanner array may be used. For example, maybe two or three or four or even five fingerprints of an individual may be simultaneously collected for deciding on the targeted output. A number of different fingerprint collection configurations may be contemplated by one skilled in the art for receiving, collecting, and/or storing fingerprints.

Alternatively, an illuminating unit/module/device may be positioned adjacent the fingerprint recognition, collection, and analysis devices 10, 50, 60, 70, 150 to illuminate the area received by the fingerprint scanner (e.g., gel-tape receiving an impression). The additional light may aid the fingerprint scanner in scanning higher quality fingerprint images.

Alternatively, more than one message may be emitted or conveyed in response to an inputted fingerprint. For example, the fingerprint analysis devices 10, 50, 60, 70, 150 may be constructed to convey 2 back-to-back messages based on the input. The fingerprint analysis devices may convey 3 messages or more. It is contemplated that the fingerprint analysis devices may convey a plurality of different messages based on one inputted fingerprint. It is also contemplated that the user may disable the sound emitting mechanism after the first message has been conveyed. It is also contemplated that the user may request more than one message after voluntarily inputting a message to activate the fingerprint analysis devices 10, 50, 60, 70, 150.

Alternatively, it is contemplated that the fingerprint analysis devices 10, 50, 60, 70, 150 may be incorporated into any product or item or display or publication or electronic device. Fingerprint analysis devices 10, 50, 60, 70, 150 may be incorporated into for example, televisions, radios, MP3 players, etc., or any other electronic device that may provide for interactive capabilities. Any electronic device may be conveniently transformed by adding a fingerprint analysis device for collecting fingerprints, analyzing the chemical composition of the fingerprints, determining the characteristics of the inputted fingerprints, and outputting targeted messaging based on the input (as discussed above with regards to the Google™ example).

Alternatively, supermarkets and/or grocery stores may recoup the initial investment of installing fingerprint analysis devices on products/items and/or shelves and/or displays and/or posters by receiving monetary rewards or discounts for each subject or consumer or individual touching the adhesive member to receive a message or advertisement or information/data. Supermarkets and/or grocery stores, such as Kroger™, Meijer™, Costco™, Safeway™, Sam's Club™, BJ's Wholesale Club™, Wal-Mart™, Kmart Super Centers™, Whole Foods Markets™, SuperValu™, A&P Supermarkets™, Waldbaum's™, Pathmark™, Piggly Wiggly™, Delhaize America™, Starbucks™, Target™, etc. and/or their affiliates/subsidiaries, may install such fingerprint analysis devices to provide further information to the public and/or to targeted individuals. However, such fingerprint analysis devices may be provided directly from the manufacturer or producer or factory or seller or promoter, or service provider, as defined below.

Alternatively, law enforcement agents may have access to a database where such fingerprint images are stored in order to compare such fingerprint images to pre-stored or prerecorded fingerprint images for the detection of persons of interest (e.g., criminals, fugitives, etc.). The law enforcement agents may determine where such criminals are located based on the collected fingerprints. Such an alternative embodiment has been contemplated in an application filed on Jun. 8, 2010, having Ser. No. 12/802,491 entitled "System and Method for Fingerprint Recognition and Collection at Points-of-Sale and Point-of-Entry," filed by the current Applicant, the contents of which are incorporated by reference herein in their entirety.

It is anticipated that such supermarkets and/or grocery stores or entertainment venues may relay fingerprint information/data to central databases for law enforcement personnel to review and analyze for detecting the location of criminals and/or persons of interest. Such fingerprint information may be relayed to a vast array of local, state, and federal authorities/agencies/bureaus, such as the FBI, CIA, NSA, Department of Homeland Security (U.S. Secret Service, U.S. Customs and Border Protection, U.S. Immigration and Customs Enforcement, etc.), Department of State, Department of Transportation, Department of Justice, etc. This is merely a non-limiting example of who may send such information and who may receive such information in such fingerprint methods and systems described herein.

As a result, law enforcement agencies may collect fingerprint data/information from a plurality of stores and/or entertainment venues across the country, continuously, in real-time, to determine where criminals/fugitives may be located. Additionally, the fingerprint data/information may be associated with time, day, and location information in order to provide law enforcement agencies with all the data/information they need to apprehend a criminal/fugitive. One skilled in the art may envision collecting, transmitting, analyzing, and storing a plurality of different data in association with fingerprint data Concerning privacy issues, it is believed that under the $4^{th}$ Amendment that privacy issues would be inapplicable in such a scenario presented in the exemplary embodiments of the present disclosure. The $4^{th}$ Amendment (Amendment IV) to the United States Constitution is the part of the Bill of Rights which guards against unreasonable searches and seizures. The question is whether voluntarily collecting fingerprints from individuals would violate the $4^{th}$ Amendment. In order to answer this question, one would pose the following inquiry: Does one have a reasonable expectation of privacy in their fingerprints? The criteria for determining if one has a reasonable expectation of privacy are as follows: 1) general legal principles; 2) the vantage point from which the surveillance is carried out; 3) the degree of privacy afforded by certain buildings and/or places; and 4) the sophistication and invasiveness of the surveillance technology employed. In the exemplary embodiments of the present disclosure, one does not have a degree of privacy in their fingerprints. By voluntarily touching things/items/products in general, one gives up their privacy to their fingerprints. Thus, the systems and methods presented herein would be compatible and in line with important legal principles and would not violate the U.S. Constitution. It is anticipated that in the exemplary embodiments of the present disclosure that the subjects or consumers or individuals voluntarily provide their fingerprint to aid the fingerprint analysis device in determining which audible or non-audible message or signal to convey.

Additionally, when implemented via executable instructions, various elements of the present disclosure are in essence the code defining the operations of such various elements. The executable instructions or code may be obtained from a readable medium (e.g., a hard drive media, optical media, EPROM, EEPROM, tape media, cartridge media, flash memory, ROM, memory stick, and/or the like) or communicated via a data signal from a communication medium (e.g., the Internet). In fact, readable media may include any medium that may store or transfer information.

The computer means may be operatively associated with the assembly, and is directed by software to compare the first output signal with a first control image and the second output signal with a second control image. The software further directs the computer to produce diagnostic output. Further, a means for transmitting the diagnostic output to an operator of the verification device is included. Thus, many applications of the present disclosure could be formulated. The exemplary network disclosed herein may include any system for exchanging data or transacting business, such as the Internet, an intranet, an extranet, WAN (wide area network), LAN (local area network), satellite communications, and/or the like. It is noted that the network may be implemented as other types of networks.

Additionally, "code" as used herein, or "program" as used herein, may be any plurality of binary values or any executable, interpreted or compiled code which may be used by a computer or execution device to perform a task. This code or program may be written in any one of several known computer languages. A "computer," as used herein, may mean any device which stores, processes, routes, manipulates, or performs like operation on data. A "computer" may be incorporated within one or more fingerprint recognition and collection systems or servers to operate one or more processors to run the fingerprint recognition algorithms. Moreover, computer-executable instructions include, for example, instructions and data which cause a general purpose computer, special purpose computer, or special purpose processing device to perform a certain function or group of functions. Computer-executable instructions also include program modules that may be executed by computers in stand-alone or network environments. Generally, program modules include routines, programs, objects, components, and data structures, etc. that perform particular tasks or implement particular abstract data types.

A service provider may be any entity that develops, offers, controls, manages, owns, alters and/or sells software and/or hardware products and/or items or products or publications. A service provider may be any entity that performs one or more tasks on one or more pre-existing fingerprint systems, which may or may not be controlled or owned by the service provider. For example, the entity may offer a service with an existing software package and/or with any type of existing Internet-based service through the Internet. In other words, a service provider need not own or provide the fingerprint systems. The fingerprint systems may be owned or provided by any third party not related or associated with the service provider. In the present disclosure, it may be contemplated that the entity (such as a service provider) may offer any type of service and/or product to optimize pre-existing, pre-owned fingerprint systems by referring potential customers to an Internet website or a store that may or may not be associated with fingerprint system-related services and/or products. The term "entity" may refer to anything that may exist as a discrete and/or distinct unit that owns, operates, manages, and/or controls one or more of a plurality of machines (such as fingerprint systems). For example, the term "entity" may include the term "company." Thus, the exemplary embodiments of the present disclosure also cover service providers of fingerprint methods and systems.

It will be understood that there are to be no limitations as to the dimensions and shape of the fingerprint systems, including the storage compartment, or the materials from which the fingerprint systems are manufactured or the electronics that may be used to run such a fingerprint system and/or fingerprint scanners (e.g., one or more biomaterials and/or biochips and/or gel biochips and/or biosensors and/or bio-electronic sensors and/or microprocessors).

The foregoing examples have been provided merely for the purpose of explanation and are in no way to be construed as limiting of the present method and system disclosed herein. While the present disclosure has been described with reference to various embodiments, it is understood that the words, which have been used herein, are words of description and illustration, rather than words of limitations. Further, although the present disclosure has been described herein with reference to particular means, materials and embodiments, the present disclosure is not intended to be limited to the particulars disclosed herein; rather, the present disclosure extends to all functionally equivalent structures, methods and uses, such as are within the scope of the appended claims. Those skilled in the art, having the benefit of the teachings of this specification, may effect numerous modifications thereto and changes may be made without departing from the scope and spirit of the present disclosure in its aspects.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

Having described the present disclosure above, various modifications of the techniques, procedures, material and equipment will be apparent to those in the art. It is intended that all such variations within the scope and spirit of the appended claims be embraced thereby.

The foregoing examples illustrate various aspects of the present disclosure and practice of the methods of the present disclosure. The examples are not intended to provide an exhaustive description of the many different embodiments of the present disclosure. Thus, although the foregoing present disclosure has been described in some detail by way of illustration and example for purposes of clarity and understanding, those of ordinary skill in the art will realize readily that many changes and modifications may be made thereto without departing form the spirit or scope of the present disclosure.

The invention claimed is:

1. A fingerprint analysis device, comprising:
a chemical analysis mechanism including an adhesive member associated with an item or product, the chemical analysis mechanism performing at least a chemical analysis of an impression of a fingerprint of a subject received directly from a finger of the subject contacting the adhesive member associated with the item or product, the chemical analysis mechanism further identifying at least a select number of molecules or molecular compounds to derive distinguishing characteristics from the impression of the fingerprint of the subject, the select number of molecules or molecular compounds used to create a chemical signature of the subject contacting the adhesive member; and
an output mechanism outputting one or more messages based on the chemical signature.

2. The device according to claim 1, wherein the adhesive member is a gel-type substance.

3. The device according to claim 1, wherein the one or more messages include additional or supplemental information related to the item or product associated with the adhesive member.

4. The device according to claim 1, wherein the one or more messages relate to advertisements or promotional information.

5. The device according to claim 1, wherein the distinguishing characteristics of the subject relate to at least one of the following: age, gender, race, dietary information, and lifestyle information or a combination thereof.

6. The device according to claim 1, wherein the one or more messages to be output are pre-recorded messages.

7. The device according to claim 1, wherein content of the one or more messages to be output is based on probabilities for matching the chemical signature of the subject with interests of the subject determined by one or more advertising/marketing entities.

8. The device according to claim 1, wherein the one or more messages to be output are updated at predetermined time intervals from remote a hub.

9. The device according to claim 1, wherein the output mechanism provides audible or visual outputs or a combination thereof.

10. The device according to claim 9, wherein the output mechanism is positioned at a point-of-entry (POE) location.

11. The device according to claim 1, wherein the impression of the fingerprint of the subject is transmitted to law enforcement personnel for comparison to fingerprints of persons of interest.

12. A method of analyzing one or more fingerprints, the method comprising:
inputting a fingerprint by contacting an adhesive member associated with an item or product;
performing, by one or more processors, all the following steps:
chemically analyzing, by a chemical analysis, an impression of the fingerprint of a subject received directly from a finger of the subject contacting the adhesive member associated with the item or product;
identifying at least a select number of molecules or molecular compounds to derive distinguishing characteristics from the impression of the fingerprint of the subject;
creating a chemical signature of the subject contacting the adhesive member from the select number of molecules or molecular compounds selected to derive the distinguishing characteristics; and
outputting one or more messages based on the chemical signature.

13. The method according to claim 12, wherein the one or more messages relate to advertisements or promotional information.

14. The method according to claim 12, wherein the distinguishing characteristics of the subject relate to at least one of the following: age, gender, race, dietary information, and lifestyle information or a combination thereof.

15. The method according to claim 12, wherein the one or more messages to be output are pre-recorded messages.

16. The method according to claim 12, wherein content of the one or more messages to be output is based on probabilities for matching the chemical signature of the subject with interests of the subject determined by one or more advertising/marketing entities.

17. The method according to claim 12, further comprising transmitting feedback information to an external source, the feedback information indicating at least one of the following:
a number of total touches of the adhesive member,
a number of age-specific touches,
a number of gender-specific touches,
a number of race-specific touches, and
a number of dietary-specific touches or a combination thereof.

* * * * *